United States Patent
Teow (10) Patent No.: US 9,408,841 B2
(45) Date of Patent: *Aug. 9, 2016

(54) COMPOSITION COMPRISING HEPATIC THERAPEUTIC ACTIVE FOR TREATING LIVER DISEASES, CERTAIN CANCERS AND LIVER HEALTH MAINTENANCE

(71) Applicant: Heptiva LLC, Rutherford, NJ (US)

(72) Inventor: Vincent I. Teow, Rutherford, NJ (US)

(73) Assignee: Heptiva LLC, Rutherford, NJ (US)

(*) Notice: Subject to any disclaimer, the term of this patent is extended or adjusted under 35 U.S.C. 154(b) by 153 days.

This patent is subject to a terminal disclaimer.

(21) Appl. No.: 14/093,111

(22) Filed: Nov. 29, 2013

(65) Prior Publication Data

US 2014/0088137 A1    Mar. 27, 2014

Related U.S. Application Data

(62) Division of application No. 13/006,457, filed on Jan. 14, 2011, now Pat. No. 8,618,125.

(51) Int. Cl.
| | | |
|---|---|---|
| A01N 43/42 | (2006.01) | |
| A61K 31/44 | (2006.01) | |
| A01N 43/82 | (2006.01) | |
| A61K 31/41 | (2006.01) | |
| A01N 43/16 | (2006.01) | |
| A61K 31/35 | (2006.01) | |
| A61K 31/473 | (2006.01) | |
| A61K 31/355 | (2006.01) | |
| A61K 31/277 | (2006.01) | |
| A61K 31/352 | (2006.01) | |
| A61K 31/382 | (2006.01) | |

(52) U.S. Cl.
CPC ............ *A61K 31/473* (2013.01); *A61K 31/277* (2013.01); *A61K 31/352* (2013.01); *A61K 31/355* (2013.01); *A61K 31/382* (2013.01)

(58) Field of Classification Search
USPC .................................. 514/297, 453
See application file for complete search history.

(56) References Cited

U.S. PATENT DOCUMENTS

| | | | |
|---|---|---|---|
| 4,101,558 A | 7/1978 | Vacek et al. | |
| 5,650,386 A | 7/1997 | Leone-Bay et al. | |
| 5,837,257 A | 11/1998 | Tsai et al. | |
| 5,916,984 A | 6/1999 | Bearson et al. | |
| 5,965,121 A | 10/1999 | Leone-Bay et al. | |
| 5,989,556 A | 11/1999 | Tsai et al. | |
| 6,136,316 A | 10/2000 | Mehrotra et al. | |
| 6,403,636 B1 | 6/2002 | Reutrakul et al. | |
| 6,455,078 B1 | 9/2002 | Wu | |
| 7,078,064 B2 | 7/2006 | Zabrecky | |
| 7,126,011 B2 | 10/2006 | Berg | |
| 7,160,896 B2 | 1/2007 | Neidle et al. | |
| 7,435,755 B2 | 10/2008 | Knopleva et al. | |
| 8,618,125 B2 | 12/2013 | Teow | |
| 2005/0142222 A1 | 6/2005 | Pan et al. | |
| 2006/0110479 A1 | 5/2006 | Mitra et al. | |
| 2007/0167441 A1 | 7/2007 | Halbrook et al. | |
| 2010/0009970 A1 | 1/2010 | Johansen et al. | |
| 2010/0048911 A1 | 2/2010 | Jiang et al. | |
| 2010/0074975 A1 | 3/2010 | Eum et al. | |
| 2010/0260875 A1 | 10/2010 | Mitra et al. | |

FOREIGN PATENT DOCUMENTS

| | | |
|---|---|---|
| WO | WO 94/05276 | 3/1994 |
| WO | WO 99/33827 | 8/1999 |
| WO | WO 2010/047633 | 4/2010 |

OTHER PUBLICATIONS

Previsani et al., "Hepatitis B," Dept. of Communicable Diseases Surveillance Response, World Health Organization (2002) at p. 6.
Previsani et al., "Hepatitis C," Dept. of Communicable Diseases Surveillance Response, World Health Organization (2002) at pp. 3 and 9.
Zhao et al., "Synthesis of Xanthones, Thioxanthones and Acridones by the Coupling of Arynes and Substituted Benzoates," J. Org. Chem. 72(2): 583-88 (2007).
Laphookhieo et al., "Cytotoxic and Antimalarial Prenylated Xanthones from Cratoxylum cochinchinense," Chem. Pharm. Bull. 54(5): 745-47 (2006).
Honda et al., "Design and Synthesis of 2-Cyano-3,12-Dioxoolean-1,9-Dien-28-Oic Acid, et al.," Bioorg. Med. Chem. Lett., 8:2711-2714, (1998).
Honda et al., "Synthetic Oleanane and Ursane Triterpenoids with Modified Rings A and C et al.," J. Med. Chem., 43:4233-4246 (2000).
Honda et al., "A Novel Dicyanotriterpenoid, 2-Cyano-3,12-Dioxoolean-1,9 (11)-Dien-28-onitrile et al.," Bioorg. Med. Chem. Lett., 12:1027-103, (2002).
Kress et al., "Triterpenoids Display Single Agent Anti-tumor Activity in a Transgenic Mouse Model et al.," PLoS one (6):e559 (Jun. 2007).
Lavhale et al., "A Novel Triterpenoid Isolated from the Root Bark of Ailanthus excelsa Roxb (Tree of Heaven), et al.," PLoS one 4(4):e5365 (Apr. 2009).
Suh et al, "A Novel Synthetic Oleanane Triterpenoid, Activity Differentiating, Antiproliferative, and Anti-Inflammatory et al.," Cancer Res. 59:336-341 (1999).
Allen et al., "Acridone," Org. Syn. 19:6 (1939).
Allen et al., "Acridone," Org. Syn. 2:15 (1943).
Luo et al., "Crystal Structure of the NS3 Protease-Helicase from Dengue Virus" J. Virol. 82(1): 173-83 (2008).
Duffy, "CA 19-9 as a Marker for Gastrointestinal Cancers: a Review," Ann. Clin. Biochem. 35( Pt 3):364-70. (1998).

(Continued)

*Primary Examiner* — Layla Soroush
(74) *Attorney, Agent, or Firm* — Eric W. Guttag; Eric W. Guttag IP Law Office (57) ABSTRACT

Compositions of hepatic therapeutic actives from one or more acridone compounds, one or more xanthone compounds, one or more thioxanthone compounds, one or more tocotrienol compounds, and one or more oleanolic triterpenoid compounds. Also, methods for treating various liver diseases or certain cancers with such hepatic therapeutic actives, as well as providing liver health maintenance.

8 Claims, 4 Drawing Sheets

(56) References Cited

OTHER PUBLICATIONS

Fernandes et al., "Hepatoprotective Activity of Xanthones and Xanthonolignoids Against tert-butylhydroperoxide-Induced Toxicity et al.," Pharm Res. 12(11):1756-60 (1995).

Fujiwara et al., "Acridone Derivatives Are Transcriptional Inhibitors of Human Immunodeficiency et al.," 11th Int'l Confer.Antivir. Res 37:A55 (abstract No. 53)(1998).

Graham et al., "Triterpenoids, Tocotrienols and Xanthones from the Bark of Cratoxylum Cochinchinense," issued on Jul. 2, 1992.

Manfroni et al.,"Inhibition of Subgenomic Hepatitis C Virus RNA Replication by Acridone Derivatives et al." J Med Chem. 52(10):3354-65 (2009).

Har et al., "Effects of Tocotrienols on Cell Viability and Apoptosis et al.," Asia Pac J Clin Nutr. 14(4):374-80 (2005).

Lien et al., "Triterpenoid and Xanthone Constituents of Cratoxylum cochinchinense," issued on Jun. 1, 1998.

International Search Report and Written Opinion of the International Search Authority (mailed Jul. 23, 2012) for PCT/US2011/062175, 12 pages.

Ren et al., "Cytotoxic and NF-kB Inhibitory Constituents of the Stems of Cratoxylum cochinchinense and Their Semisynthetic Analogues," J. Nat. Prod., vol. 74 (2011) pp. 1117-1125.

Ryu et al., "Oleanane Triterpenoid CDDO-Me Induces Apoptosis in Multidrug Resistant Osteosarcoma Cells through Inhibition of Stat3 Pathway," BMC Cancer 10:187 (2010).

Elliot et al., "The Triterpenoid CDDO Inhibits Expression of Matrix Metalloproteinase-1, Matrix Metalloproteinase-13 and Bcl-3 et al.," Arthritis Res. Ther. 5:R285-91 (2003).

Honda et al., "Novel Tricyclic Compounds Having Acetylene Groups at C-8a and Cyano Enones in Rings A and C et al.," J. Med. Chem. 50(8):1731-34 (2007).

Chintharlapalli et al., "2-Cyano-3,12-dioxooolean-1,9-dien-28-oic Acid (CDDO) and Related Compounds et al.," Mol. Pharm Fast Forward MOL 105:11437 (Mar. 29, 2005).

Place et al., "The Novel Synthetic Triterpenoid, CDDO-Imidazolide, Inhibits Inflammatory Response and Tumor Growth in Vivo," Clinical Cancer Res. 8:2798 (2003).

Tran et al., "The Synthetic Triterpenoid CDDO-Methyl Ester Modulates Microglial Activities, Inhibits TNF Production et al.," J. Neuroinflammation 5:14 (2008).

Sun et al., "Structure-Activity Relationships of Oleanane- and Ursane-Type Triterpenoids," Botanical Studies 47:339-68 (2006).

Kinoshita et al., "First Synthesis of (1)-a- and (1)-g—Polypodatetraenes," Chem. Pharm. Bull. 50(7):930-34 (2002).

Liu et al., "Synthesis and Tumor Cytotoxicity of Novel Amide Derivatives of β-Hederin," Molecules 15:7871-83 (2010).

Tang, "Folk Medicine-Cratoxylum cochinchinesnse Antioxidant but Cytotoxic," Thesis Submitted to National University of Singapore (2005).

Lockhart et al., "A Phase I Dose-Escalation Study of SR271425 et al." Am. J. of Clin. Oncology 32(1):9-14 (2009).

Phuwapraisirisan et al., "Antioxidant Xanthones from Cratoxylum cochinchinense" National Product Res. 14:1332-37 (2006).

Stevenson et al., "Phase I/Pharmacokinetic Trial of the Novel Thioxanthone SR233377 (WIN33377) on a 5-day Schedule," Cancer Chemother Pharmacol. 44(3):228-34 (1999).

Sen et al., "Tocotrienols: Vitamin E Beyond Tocopherols". Life Sci. 78 (18):2088-98 (2006).

Tang et al., "Mechanism of Cell Death Induced by an Antioxidant Extract of Cratoxylum cochinchinense et al.," Free Radic Biol Med. 36(12):1588-611. (2004).

To et al., "Synthetic Triterpenoids %arget the Arp2/3 Complex and Inhibit Branched Actin Polymerization." J. Biol. Chem. 285(36):27944-57 (2010).

Venugopal et al., "Novel in Vitro Model Barriers for Evaluation of the Permeability of Antitumor Compounds, Thioxanthones," Investigational New Drugs 24:2111-16 (2006).

COMPOSITION COMPRISING HEPATIC THERAPEUTIC ACTIVE FOR TREATING LIVER DISEASES, CERTAIN CANCERS AND LIVER HEALTH MAINTENANCE

CROSS-REFERENCE TO RELATED APPLICATIONS

This application is a divisional of U.S. application Ser. No. 13/006,457 filed Jan. 14, 2011. The entire disclosure and contents of the above referenced application is hereby incorporated by reference.

FIELD OF THE INVENTION

The present invention broadly relates to compositions comprising hepatic therapeutic actives comprising one or more acridone compounds, one or more xanthone compounds, one or more thioxanthone compounds, one or more tocotrienol compounds, and one or more oleanolic triterpenoid compounds. The present application also relates to treating various liver diseases with such hepatic therapeutic actives. The present application further relates to treating cancers indicated by the CA19-9 cancer marker with such hepatic therapeutic actives. The present application additionally relates to using such hepatic therapeutic actives for liver health maintenance.

BACKGROUND

Hepatitis is a general term referring to an inflammation of the liver and may be caused by several mechanisms, including infectious agents. Viral hepatitis may be triggered by a variety of different viruses such as hepatitis B, and hepatitis C. Since the development of jaundice is a characteristic feature of liver disease and not just viral hepatitis, a correct diagnosis may only be made by testing patients' blood for the presence of specific anti-viral antibodies.

Hepatitis B is a potentially life-threatening liver infection caused by the hepatitis B virus. It is a major global health problem and the most serious type of viral hepatitis. Hepatitis B virus (HBV) may cause an acute illness with symptoms that last several weeks, including yellowing of the skin and eyes (jaundice), dark urine, extreme fatigue, nausea, vomiting and abdominal pain, etc. Afflicted individuals may take several months to a year to recover from the symptoms. HBV may also cause a chronic liver infection that may later develop into cirrhosis of the liver or liver cancer, thus putting individuals afflicted with HBV at a high risk of death from cirrhosis of the liver and liver cancer. Worldwide, an estimated two billion people have been infected with HBV, and more than 350 million have chronic (long-term) liver infections. See Previsani et al., "Hepatitis B," *Dept. of Communicable Diseases Surveillance Response, World Health Organization* (2002) at page 6.

A vaccine against hepatitis B has been available since 1982. This hepatitis B vaccine is 95% effective in preventing HBV infection and its chronic consequences, including potentially liver cancer. Unfortunately, the potency of this hepatitis B vaccine decreases and wears off over time. In addition, this hepatitis B vaccine is only effective if the person receives this vaccine before the onset HBV infection. In other words, this vaccine cannot be used to treat a person who is already infected with HBV.

Hepatitis C infections are often asymptomatic, but once established, chronic infections may progress to scarring of the liver called fibrosis, as well as advanced scarring (i.e., cirrhosis). In some cases, those with cirrhosis may develop further complications from hepatitis C infections, including hepatocellular carcinoma (HCC). See Previsani et al., "Hepatitis C," *Dept. of Communicable Diseases Surveillance Response, World Health Organization* (2002) at pages 3 and 9. Currently there is no effective vaccination against hepatitis C. One reason for no currently effective vaccination against hepatitis C is that this virus may come in many forms and may constantly mutate, thus leading to "swarms" of closely related viral genomic sequences (which are referred to as "quasispecies").

About 25% of those persons with human immunodeficiency virus (HIV), primarily those who acquired HIV through injection drug use or through a blood transfusion, may also be infected with hepatitis HBV or HCV. Hepatitis B or hepatitis C infections may progress very quickly in HIV-positive people. This co-infection of HIV and hepatitis B or hepatitis C may thus complicate the treatment of affected individuals. For example, people with liver damage due to chronic hepatitis are more likely to experience hepatotoxicity (liver toxicity) related to anti-HIV drugs. In addition, anti-HIV drugs and anti-hepatitis drugs may interact and cause an exacerbation of side effects.

Many experts recommend that HIV should be controlled first before a person begins treatment against viruses such as HBV or HCV. With extremely careful management, people with HIV/HBV or HIV/HCV co-infection may be successfully treated for both diseases. Even so, such careful management treatments may be difficult to carry out because of the need to balance the administration of anti-HIV drugs versus anti-HBV/HCV drugs, e.g., to avoid hepatotoxicity related to anti-HIV drugs, as well as adverse interactions between anti-HIV drugs and anti-HBV/HCV drugs.

SUMMARY

According to a first broad aspect of the present invention, there is provided a composition comprising a hepatic therapeutic amount of a hepatic therapeutic active having, by weight of the hepatic therapeutic active:

from about 25 to about 35% of one or more acridone compounds;

from about 15 to about 25% of one or more xanthone compounds;

from about 35 to about 45% of one or more thioxathone compounds;

from about 1 to about 10% of one or more tocotrienol compounds; and from about 1 to about 10% of one or more oleanolic triterpenoid compounds.

According to a second broad aspect of the present invention, there is provided a method comprising the following steps:

(a) providing a hepatic therapeutic active having, by weight of the hepatic therapeutic active: from about 25 to about 35% of one or more acridone compounds; from about 15 to about 25% of one or more xanthone compounds; from about 35 to about 45% of one or more thioxathone compounds; from about 1 to about 10% of one or more tocotrienol compounds; and from about 1 to about 10% of one or more oleanolic triterpenoid compounds; and (b) administering a hepatic therapeutic amount of the hepatic therapeutic active to a patient afflicted with a liver disease.

According to a third broad aspect of the present invention, there is provided a method comprising the following steps:

(a) providing a hepatic therapeutic active having, by weight of the hepatic therapeutic active: from about 25 to about 35% of one or more acridone compounds; from about 15 to about 25% of one or more xanthone compounds; from about 35 to about 45% of one or more thioxathone compounds; from about 1 to about 10% of one or more tocotrienol compounds; and from about 1 to about 10% of one or more oleanolic triterpenoid compounds; and (b) administering a therapeutic amount of the hepatic therapeutic active to a mammal afflicted with a CA19-9 cancer.

According to a fourth broad aspect of the present invention, there is provided a method comprising the following steps:

(a) providing a hepatic therapeutic active having, by weight of the hepatic therapeutic active: from about 25 to about 35% of one or more acridone compounds; from about 15 to about 25% of one or more xanthone compounds; from about 35 to about 45% of one or more thioxathone compounds; from about 1 to about 10% of one or more tocotrienol compounds; and from about 1 to about 10% of one or more oleanolic triterpenoid compounds; and (b) administering a liver health maintenance amount of the hepatic therapeutic active to a human in need of liver health maintenance.

BRIEF DESCRIPTION OF THE DRAWINGS

The invention will be described in conjunction with the accompanying drawings, in which.

DETAILED DESCRIPTION

It is advantageous to define several terms before describing the invention. It should be appreciated that the following definitions are used throughout this application.

Definitions

Where the definition of terms departs from the commonly used meaning of the term, applicant intends to utilize the definitions provided below, unless specifically indicated.

For the purposes of the present invention, the term "hepatic therapeutic active" (along with the term "hepatic therapeutic drug") refers to the component which comprises the acridone compounds, xanthone compounds, thioxanthone compounds, tocotrienol compounds, and oleanolic triterpenoid compounds, and which is therapeutically active in treating the liver diseases and certain cancers described herein. The hepatic therapeutic active may be prepared, formed, etc., from one or more plant extracts (e.g., plant extracts obtained from plant materials which include one or more of the stem, bark, roots, etc., of the *Cratoxylum cochinchinense* plant by using one or more of an aqueous solvent, such as water, a polar organic solvent, such as ethanol, or a non-polar organic solvent such as hexane); by combining the acridone compounds, xanthone compounds, thioxanthone compounds, tocotrienol compounds, and oleanolic triterpenoid compounds through blending, mixing, etc., of separately synthesized compounds (or mixtures of synthesized compounds) and/or on compounds obtained from such plant extracts, etc.

For the purposes of the present invention, the term "acridone compounds" refers to one or more compounds having the acridone chemical structure, such as those having the following general formula I:

wherein each of the $R_{11}$, $R_{12}$, $R_{13}$, $R_{14}$, $R_{15}$, $R_{16}$, $R_{17}$, or $R_{18}$ groups separately may be an H, hydroxy, halo, amino, sulfoxy, or aliphatic group; and wherein the $R_{19}$ group may be an H or aliphatic group. Acridone compounds may include one or more of: acridone (9,10-dihydro-9-oxoacridine, wherein all $R_{11}$, $R_{12}$, $R_{13}$, $R_{14}$, $R_{15}$, $R_{16}$, $R_{17}$, or $R_{18}$ groups are H and wherein $R_{19}$ is H), acridone acetic acid (wherein $R_{11}$, $R_{12}$, $R_{13}$, $R_{14}$, $R_{15}$, $R_{16}$, $R_{17}$, or $R_{18}$ groups are H, and wherein $R_{19}$ is COOH), etc. Acridone compounds may be obtained, for example, from *Cratoxylum cochinchinense* extracts. Acridone compounds may also be obtained synthetically, for example, by acid-induced ring closure of N-phenyl anthranilic acids; by the reaction of silylaryl triflates, CsF and ortho heteroatom-substituted benzoates; etc. See Zhao et al., "Synthesis of Xanthones, Thioxanthones and Acridones by the Coupling of Arynes and Substituted Benzoates," *J. Org. Chem.* 72(2): 583-88 (2007), the entire contents and disclosure of which is herein incorporated by reference. The acridone compounds are at least one of the anti-viral components in the hepatic pharmaceutical active which are believed to function by inhibiting the growth and multiplication of the chronic hepatitis HBV and chronic hepatitis HCV in patients afflicted with chronic hepatitis B and chronic hepatitis C.

For the purposes of the present invention, the term "xanthone compounds" refers to one or more compounds having the xanthone chemical structure, such as those having the following general formula II:

wherein each of the $R_{21}$, $R_{22}$, $R_{23}$, $R_{24}$, $R_{25}$, $R_{26}$, $R_{27}$, or $R_{28}$ groups separately may be an H, hydroxy, halo, amino, sulfoxy, or aliphatic group. Xanthone compounds may include one or more of: xanthone (9H-xanthen-9-one, wherein all the $R_{21}$, $R_{22}$, $R_{23}$, $R_{24}$, $R_{25}$, $R_{26}$, $R_{27}$, or $R_{28}$ groups are H); 5-O-methylcelebixanthone (wherein the $R_{21}$ group is isopentenyl, the $R_{22}$ group is methoxy, the $R_{23}$ group is hydroxy, the $R_{24}$ group is methoxy, and all of $R_{25}$, $R_{26}$, $R_{27}$, and $R_{28}$ groups are H); celebixanthone (wherein the $R_{21}$ group is isopenten- 2-yl, the $R_{22}$ group is methoxy, the $R_{23}$ and $R_{24}$ group are hydroxy, and all of $R_{25}$, $R_{26}$, $R_{27}$, and $R_{28}$ groups are H); 1,3,7-trihydroxy-2,4-di(3-methylbut-2-enyl)xanthone (wherein the $R_{21}$ group is isopentenyl, the $R_{22}$ group is methoxy, the $R_{23}$ and $R_{24}$ groups are H, the $R_{25}$ group is isopenten-2-yl, the $R_{26}$ group is hydroxy, the $R_{27}$ group isopenten-2-yl, and the $R_2$ group is hydroxy); cochinchinone A (wherein the $R_{21}$ group is isopent-2-enyl, the $R_{22}$ group is methoxy, the $R_{23}$ and $R_{24}$ groups are H, the $R_{25}$ group is 3,7-dimethyl-2,6-diene-yl, the $R_{26}$ group is hydroxy, the $R_{27}$ group isopenten-2-yl, and the $R_{28}$ group is hydroxy), alpha-mangostin (wherein the $R_{21}$ group is isopenten-2-yl, the $R_{22}$ group is methoxy, the $R_{23}$ group is hydroxy, the $R_{24}$ group is H, the $R_{25}$ group is H, the $R_{26}$ group is hydroxy, the $R_{27}$ group is isopenten-2-yl, and the $R_{28}$ group is hydroxy); beta-mangostin (wherein the $R_{21}$ group is isopenten-2-yl, the $R_{22}$ group is methoxy, the $R_{23}$ group is hydroxy, the $R_{24}$ group is H, the $R_{25}$ group is H, the $R_{26}$ group is methoxy, the $R_{27}$ group is isopenten-2-yl, and the $R_{28}$ group is hydroxy); cochinchinone; etc. Xanthone compounds may be obtained, for example, from *Cratoxylum cochinchinense* extracts. See Laphookhieo et al., "Cytotoxic and Antimalarial Prenylated Xanthones from *Cratoxylum cochinchinense*," *Chem. Pharm. Bull.* 54(5): 745-47 (2006). Xanthone compounds may also be obtained synthetically, for example, by self-condensation of N-phenylanthranilic acid; by the reaction of silylaryl triflates, CsF and ortho heteroatom-substituted benzoates; etc. See Zhao et al., "Synthesis of Xanthones, Thioxanthones and Acridones by the Coupling of Arynes and Substituted Benzoates," *J. Org. Chem.* 72(2): 583-88 (2007), the entire contents and disclosure of which is herein incorporated by reference. The xanthone compounds are at least one of the anti-viral components in the hepatic pharmaceutical active which are believed to function by exhibiting hepatoprotective activity and antitumor properties that protect the liver from further damage caused by hepatitis HBV and HCV viruses.

For the purposes of the present invention, the term "thioxanthone compounds" refers to one or more compounds having a thioxanthone chemical structure, such as those having the following general formula II:

III wherein each of the $R_{31}$, $R_{32}$, $R_{33}$, $R_{34}$, $R_{35}$, $R_{36}$, $R_{37}$, or $R_{38}$ groups separately may be an H, hydroxy, halo, amino, sulfoxy, or aliphatic group. Thioxanthone compounds may include one or more of: thioxanthone (9-oxothioxanthene or thioxanthen-9-one, wherein all the $R_{31}$, $R_{32}$, $R_{33}$, $R_{34}$, $R_{35}$, $R_{36}$, $R_{37}$, or $R_{38}$ groups are H); the thio analogs of 5-O-methylcelebixanthone, celebixanthone, 1,3,7-trihihydroxy-2,4-di(3-methylbut-2-enyl)xanthone, cochinchinone A, alpha-mangostin, beta-mangostin, and cochinchinone; etc. Thioxanthone compounds may be obtained from *Cratoxylum cochinchinense* extracts. Thioxanthone compounds may also be obtained synthetically, for example, by the reaction of silylaryl triflates, CsF and ortho heteroatom-substituted benzoates; by reacting an aromatic compound such as cumene with a thiosalicyclic acid or dithiosalicylic acid in the presence of sulfuric acid; by reacting a mixture of a 2-chlorothiobenzoyl chloride and a substituted or unsubstituted benzene using a Friedel-Crafts catalyst; etc. See, for example, Zhao et al., "Synthesis of Xanthones, Thioxanthones and Acridones by the Coupling of Arynes and Substituted Benzoates," *J. Org. Chem.* 72(2): 583-88 (2007); U.S. Pat. No. 5,916,984 (Bearson et al.), issued Jun. 29, 1999; U.S. Pat. No. 7,126,011 (Berg), issued Oct. 24, 2006; U.S. Pat. No. 4,101,558 (Vacek et al.), issued Jul. 18, 1978, the entire contents and disclosure of which are herein incorporated by reference. The thioxanthone compounds are at least one of the anti-viral components in the hepatic pharmaceutical active which are believed to function by suppressing tumor and cancer cell growth.

For the purposes of the present invention, the term "tocotrienol compounds" refers to one or more compounds having the tocotrienol chemical structure, such as those having the following general formula IV:

IV wherein each of the $R_{41}$, $R_{42}$, $R_{43}$, and $R_{44}$ groups separately may be an H, hydroxy, halo, amino, sulfoxy, or aliphatic group. Tocotrienol compounds may include one or more of: alpha-tocotrienol (wherein all of the $R_{41}$, $R_{42}$, $R_{43}$, and $R_{44}$ groups are methyl); beta-tocotrienol (wherein the $R_{42}$ group is H, and the $R_{41}$, $R_{43}$, and $R_{44}$ groups are each methyl); gamma-tocotrienol (wherein the $R_{41}$ group is H, and the $R_{42}$, $R_{43}$, and $R_{44}$ groups are each methyl); delta-tocotrienol (wherein the $R_{41}$ and $R_{42}$ groups are each H, and the $R_{43}$ and $R_{44}$ groups are each methyl); etc. Tocotrienol compounds may be obtained from *Cratoxylum cochinchinense* extracts; may be obtained from tocotrienol-enriched fractions derived from vegetable oils (e.g., those vegetable oils derived from sunflower seed, palm, wheat germ, bran, barley, brewer's grain oats, etc); etc.; from tocotrienol-enriched vitamin E preparations and fractions, etc. The tocotrienol compounds are believed to function in the hepatic pharmaceutical active as an antioxidant and to reduce cell viability in liver cancer cells, potentially by apotosis.

For the purposes of the present invention, the term "oleanolic triterpenoid compounds" refers to one or more compounds having a chemical structure the same as, or structurally analogous to, oleanolic acid, and which may include oleanolic acid, as well as derivatives of oleanolic acid, such as glycosylated derivatives of oleanolic acid (oleanolic acid saponins such as beta-hederin), as well as derivatives of oleanolic acid having the following general formula V:

V wherein $M_1$ may be H or an alkali metal (e.g., sodium, potassium, etc.); wherein $M_2$ may be H, an alkali metal (e.g., sodium, potassium, etc.) aliphatic group, or aromatic group (including heterocyclic aromatic groups, such as imidazolyl); and wherein each of $R_{51}$, $R_{52}$, $R_{53}$, $R_{54}$, $R_{55}$, or $R_{56}$, separately may be an H, hydroxy, halo, amino, sulfoxy, or aliphatic group; or derivatives having the following general formula VI:

VI wherein $M_3$ may be H, an alkali metal (e.g., sodium, potassium, etc.), an aliphatic group, or an aromatic group (including heterocyclic aromatic groups, such as imidazolyl); and wherein each of $R_{61}$, $R_{62}$, $R_{63}$, $R_{64}$, $R_{65}$, $R_{66}$, or $R_{67}$, separately may be an H, hydroxy, halo, amino, sulfoxy, or aliphatic group. The oleanolic triterpenoid compounds of formulas V and VI may include one or more of: 3-hydroxy-23-sulfoxy-olean-12-en-28-oic acid (wherein all of the $M_1$ or $M_2$ groups are H and wherein all of the $R_{51}$, $R_{52}$, $R_{53}$, $R_{54}$, $R_{55}$, and $R_{56}$ group are methyl; 2-cyano-3,12-dioxooleana-1,9 (11)-dien-28-oic (CDDO, wherein the $M_3$ group is H and all of the $R_{61}$, $R_{62}$, $R_{63}$, $R_{64}$, $R_{65}$, $R_{66}$, and $R_{67}$ groups are methyl), the respective methyl ester of CDDO (CDDO-Me, wherein $M_3$ is methyl), and the respective imidazolide of CDDO (CDDO-Im, wherein $M_3$ is imidazolyl); etc. The oleanolic triterpenoid compounds may be obtained from natural plant extracts. For example, 3-hydroxy-23-sulfoxy-olean-12-en-28-oic acid may be obtained from *Cratoxylum cochinchinense* extracts; etc. The oleanolic triterpenoid compounds may also be obtained synthetically. For example, CDDO, CDDO-Me and CDDO-Im may be obtained by the synthetic methods described in U.S. Pat. No. 7,435,755 (Konopleva et al.), issued Oct. 14, 2008; Honda et al., "Design and Synthesis of 2-Cyano-3,12-Dioxoolean-1,9-Dien-28-Oic Acid, a Novel and Highly Active Inhibitor of Nitric Oxide Production in Mouse Macrophages," *Bioorg. Med. Chem. Lett.,* 8:2711-2714, (1998); Honda et al. "Synthetic Oleanane and Ursane Triterpenoids with Modified Rings A and C: a Series of Highly Active Inhibitors of Nitric Oxide Production in Mouse Macrophages," *J. Med. Chem.,* 43:4233-4246 (2000); Honda et al., "A Novel Dicyanotriterpenoid, 2-Cyano-3,12-Dioxooleana-1.9(11)-Dien-28-onitrile, Active at Picomolar Concentrations for Inhibition of Nitric Oxide Production" *Bioorg. Med. Chem. Lett.,* 12:1027-103, (2002), the entire contents and disclosures of which are herein incorporated by reference. The oleanolic triterpenoid compounds are believed to function in the hepatic pharmaceutical active as an anti-inflammatory by, for example, aiding in the repair of damaged liver cells due to chronic hepatitis B, chronic hepatitis C, or hepatocellular carcinoma (HCC).

For the purposes of the present invention, the term "aliphatic" refers to a carbon-containing moiety other than an aromatic moiety. Aliphatic moieties may be straight chain, branched chain, cyclic (cycloaliphatic), or any combination thereof, may be substituted or unsubstituted, may include one or more heteroatoms (e.g., oxygen atoms, nitrogen atoms, sulfur atoms, etc.) in the carbon chain (i.e., may be heterocyclic), may be unsaturated (i.e., one, two or more double bonds) or saturated, etc., and may have any desired number of carbon atoms, e.g., from 1 to 30 carbon atoms, for example from 1 to 12 carbon atoms, such as from 1 to 6 carbon atoms (e.g., from 1 to 4 carbon atoms), etc. Aliphatic moieties suitable herein may include, but are not limited to, substituted or unsubstituted alkyl, alkenyl, alkadienyl, alkynyl, cycloalkyl, cycloalkenyl, alkoxy, etc. Suitable aliphatic moieties may include, but are not limited to, alkyl (e.g., methyl, ethyl, propyl, butyl, pentyl, hexyl, heptyl, octyl, nonyl, decyl, dodecyl, etc.) and substituted alkyl (e.g., hydroxylmethyl, hydroxyethyl, trifluoromethyl, alkoxymethyl, etc.), alkoxy (e.g., methoxy), carboxy, ester, amide, sulfonamide, carbamate, acyl (i.e., aldehyde or keto), etc., or any combination thereof.

For the purposes of the present invention, the term "aromatic" refers to an unsaturated cyclic arene moiety containing one or more unsaturated cyclic rings (for example, 5 and/or 6 atoms per ring) that can be substituted, unsubstituted, or a combination thereof, can be heterocyclic (i.e., including one or more oxygen atoms, nitrogen atoms, sulfur atoms, etc.), nonheterocyclic, or a combination thereof, can have any desired number of carbon atoms, e.g., from 3 to 30 carbon atoms, for example, from 3 to 18 carbon atoms, e.g., from 3 to 12 carbon atoms, etc. Aromatic moieties suitable herein can include, but are not limited to, substituted or unsubstituted phenyl, naphthyl, biphenyl, binaphthyl, phenanthenryl, anthracenyl, pyridinyl, pyrimidinyl, purinyl, pyrinyl, furanyl, thiophenyl, benzofuranyl, benzothiophenyl, dibenzofuranyl, dibenzothiophenyl, imidazolyl, oxazolyl, thiazolyl, pyrazolinyl, indolyl, pyridazinyl, pyrazinyl, quinolinyl, isoquinolinyl, benzoquinolinyl, phenanthrolinyl (e.g., 1,10-phenanthrolyl), carbazolyl, etc. Suitable aromatic moieties may include, but are not limited to, halo (i.e., fluoro, chloro, bromo, iodo), alkyl (e.g., methyl, ethyl, propyl, butyl, etc.) and substituted alkyl (e.g., hydroxymethyl, hydroxyethyl, trifluoromethyl, alkoxymethyl, etc.), amino and substituted amino (e.g., dimethylamino, etc.), hydroxy (e.g. a phenol), carboxy, sulfonate, ester, amide, sulfonamide, carbamate, acyl (i.e., aldehyde or ketone), nitro, etc., or any combination thereof.

For the purposes of the present invention, the term "halo group" refers to a fluoro substituent, a chloro substituent, a bromo substituent, an iodo substituent, or mixture thereof.

For the purpose of the present invention, the term "*Cratoxylum cochinchinense*" refers to flowering plants belonging to the Guttiferae or Clusiaceae family which may be found in Brunei, China, India, Indonesia, Malaysia, Myanmar, the Philippines, Singapore, Thailand, Vietnam, etc.

For the purpose of the present invention, the term "*Cratoxylum cochinchinense* extract" refers to one or more extracts obtained from one or more of the plant materials, e.g., bark, stem, root, etc., of the *Cratoxylum cochinchinense* plant.

For the purposes of the present invention, the term "liver disease" (along with the term "hepatic disease") refers to various diseases affecting the liver which may be caused by viruses, cancers, hepatotoxic agents (e.g., alcohol, acetaminophen, etc.), etc., and which may include hepatitis, such as acute or chronic hepatitis B, acute or chronic hepatitis C, etc.; cirrhosis (e.g., alcohol induced cirrhosis, cirrhosis induced by chronic hepatitis C, etc.); liver poisoning caused hepatotoxic agents such as alcohol, acetaminophen, etc.; cancers of the liver (e.g., hepatocellular carcinoma (HCC), also referred to as malignant hepatoma, cholangiocarcinoma (CAC), etc.); co-infections of the liver caused by Human immunodeficiency virus (HIV) and hepatitis B and/or C viruses (e.g., hepatitis HBV, hepatitis HCV, etc.), etc.

For the purposes of the present invention, the term "hepatitis" refers to various inflammations of the liver (e.g., hepatitis B, hepatitis C, etc.) which may be caused, for example, by hepatitis B virus (hepatitis HBV), hepatitis C virus (hepatitis HCV), hepatotoxic agents, etc.

For the purposes of the present invention, the terms "HBV DNA" or "HBV" refer interchangeably to hepatitis B virus.

For the purposes of the present invention, the terms HCV DNA" or "HCV" refer interchangeably to hepatitis C virus.

For the purposes of the present invention, the term "therapeutic amount" may refer to either an amount of the hepatic therapeutic active which is effective to treat a liver disease of the afflicted patient or an amount of the hepatic therapeutic active which is effective to treat a CA19-9 cancer of the afflicted patient.

For the purposes of the present invention, the term "hepatic therapeutic amount" refers to an amount of the hepatic therapeutic active which is effective to treat a liver disease of the afflicted patient.

For the purposes of the present invention, the term "liver health maintenance amount" refers to an amount of the hepatic therapeutic active which is effective to provide a measurable benefit in terms of liver health of to a human in need of liver health maintenance. Such liver health maintenance may include preventing contraction of liver diseases and/or cancers, improving, sustaining, maintaining, etc., general liver health, etc.

For the purposes of the present invention, the term "treating" refers to administration of the hepatic therapeutic active to a patient for the purpose of inhibiting, arresting, reducing, impeding, curing, stopping, slowing, checking, combating, suppressing, preventing, etc., the effects of liver disease (or CA19-9 cancer) afflicting that patient, as well as symptoms induced by such effects, for example, fatigue, stomach bloating sensations, ascites (i.e., the accumulation of fluid in the peritoneal cavity), anorexia, etc. These effects of liver disease may include neoplastic effects in the liver (e.g., tumor growth), inflammation of the liver and surrounding tissues, carcinomas of the liver and surrounding tissues and/or organs, liver cell damage, etc.

For the purposes of the present invention, the term "pharmaceutically acceptable salt" means non-toxic salts of the compounds present in the hepatic therapeutic active (which are generally prepared by reacting the free acid with a suitable organic or inorganic base) and include, but are not limited to, the acetate, benzalkonium, benzenesulfonate, benzoate, bicarbonate, bisulfate, bitartrate, borate, bromide, calcium, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandlate, mesylate, methylbromide, methylnitrate, methylsulfate, mucate, napsylate, nitrate, oleate, oxalate, pamaote, palmitate, panthothenate, phosphate, diphosphate, polygalacturonate, salicylate, stearate, subacetate, succinate, tannate, tartrate, teoclate, tosylate, triethiodide, and valerate salts, as well as mixtures of these salts.

For the purposes of the present invention, the term "mammal" includes primates (e.g., humans, monkeys, etc.), dogs, rabbits, rats, mice, hamsters, guinea pigs, and other species commonly known to be mammals.

For the purposes of the present invention, the term "patient" refers to a mammal (e.g., human) who is afflicted with one or more liver diseases or cancers.

For the purposes of the present invention, the term "U/L," when measuring, testing, analyzing, etc., for components in body fluid (e.g., blood) samples from patients refers to units per liter, while the term "U/ml," when measuring, testing, analyzing, etc., for components in body fluid (e.g., blood) samples from patients refers to units per milliliter.

For the purposes of the present invention, the term "ALT" refers to Alanine Transaminase Liver enzyme (also called Serum Glutamic Pyruvate Transaminase (SGPT) or Alanine aminotransferase (ALAT)), which is an enzyme present in hepatocytes (liver cells) and for which detection of a dramatic rise in level rise signals acute liver damage.

For the purposes of the present invention, the term "AST" refers to Aspartate Transaminase Liver enzyme (also called Serum Glutamic Oxaloacetic Transaminase (SGOT) or Aspartate aminotransferase (ASAT)), which is another enzyme associated with liver parenchymals and for which detection of a dramatic rise in level also signals acute liver damage.

For the purposes of the present invention, the term "HBsAg" refers to Hepatitis B Surface Antigen which is associated with hepatitis B virus (HBV) and which, if detected in an antigen test, indicates the presence of/infection by HBV.

For the purposes of the present invention, the term "HBeAg" refers to Hepatitis B "e" Antigen, which is a splice variant of HBcAg (core antigen), and which, if detected, indicates the presence of/infection by HBV.

For the purposes of the present invention, the term "Anti-HCV (EIA-3)" refers to Anti-Hepatitis C Antibody HCV RNA-Hepatitis C Virus, which is an anti-HCV antibody which may be detected by an EIA-3 enzyme immunoassay, and which, if detected, indicates the presence of/infection by HCV.

For the purposes of the present invention, the terms "CA19.9" and "CA 19-9) refer interchangeably to the Carbohydrate Antigen 19-9, a monoclonal antibody generated by cancerous cells which may be used as a cancer marker for certain carcinomas (cancers), and which, if detected in elevated levels, may indicate the presence of cancer(s).

For the purposes of the present invention, the term "CA19-9 cancer" refers to a cancer which may be indicated by a CA19-9 cancer marker. Such CA19-9 cancers may include one or more of: liver cancer, gastric cancer, pancreatic cancer, colorectal cancer (e.g., colon cancer), bile duct cancer, esophageal cancer, gastro intestinal tract cancer, etc.

For the purposes of the present invention, the term "comprising" means various components and steps can be conjointly employed in the present invention. Accordingly, the term "comprising" encompasses the more restrictive terms "consisting essentially of" and "consisting of."

For the purposes of the present invention, all amounts, parts, ratios and percentages used herein are by weight unless otherwise specified.

Description

Solvent extraction of *Cratoxylum cochinchinense* according extraction processes described herein has provided extracts which, through phytochemical testing, reveal the presence of five classes of therapeutic compounds which, in combination, are therapeutically active in treating various liver diseases. These five classes of therapeutic compounds are acridone compounds, xanthone compounds, thioxanthone compounds, tocotrienol compounds, and oleanolic triterpenoid compounds. Embodiments of the hepatic therapeutic actives according to the present invention may comprise, by weight of the active: from about 25 to about 35% (e.g., from about 28 to about 32%) of one or more acridone compounds; from about 15 to about 25% (e.g., from about 18 to about 22%) of one or more xanthone compounds; from about 35 to about 45% (e.g., from about 38 to about 42%) of one or more thioxanthone compounds; from about 1 to about 10% (e.g., from about 3 to about 7%) of one or more tocotrienol compounds; and from about 1 to about 10% (e.g., from about 3 to about 7%) of one or more oleanolic triterpenoid compounds. These hepatic therapeutic actives may be formulated, prepared, etc., from one or more extracts obtained from, for example, the bark, stem, root, etc., of the plant *Cratoxylum cochinchinense*; may be formulated, prepared, etc., by combining, mixing, blending, etc., together synthesized acridone compounds, xanthone compounds, thioxanthone compounds, tocotrienol compounds, and oleanolic triterpenoid compounds; may be formulated, prepared, etc., by combining, mixing, blending, etc., together one or more *Cratoxylum cochinchinense* plant extracts comprising one or more of these acridone compounds, xanthone compounds, thioxanthone compounds tocotrienol compounds, and oleanolic triterpenoid compounds, with synthetically obtained sources of one or more of these compounds, etc.

In one embodiment of a process for obtaining the hepatic therapeutic active, plant materials (e.g., bark, stem, root, etc.) from the *Cratoxylum cochinchinense* materials may be used which have, for example, been dried (e.g., air dried). These dried plant materials may then be subjected to three sequential extractions steps. In the first extraction step (aqueous extraction), these dried plant materials are extracted with an aqueous solvent (e.g., water, in for example, a w/v ratio of plant materials:water of from about 1:5 to about 1;15, such as from about 1:8 to about 1:12) for a period of, for example, at least about 30 minutes to provide a first (water-soluble) filtrate. In the second extraction step (polar organic solvent extraction), the residual plant materials from the first extraction are extracted again with a polar organic solvent (e.g., ethanol in, for example, a v/v ratio of plant materials:ethanol of about 1:35 to about 1;45, such as from about 1:38 to about 1:42) for a period of for example, at least about 60 minutes. In a third extraction step (non-polar organic solvent extraction), the residual plant materials from the second extraction are extracted again with a non-polar organic solvent (e.g., hexane, in for example, a v/v ratio of plant materials:hexane of from about 1:2 to about 1:4, such as from about 1:2.5 to about 1;3.5) for a period of for example, at least about 60 minutes. The three filtrates resulting from these three sequential extraction steps may then be combined together to provide the hepatic therapeutic active. The resulting combined hepatic therapeutic active may be further processed (e.g., lyophilized (freeze dried)) to provide the hepatic therapeutic active for use in treating a liver disease.

Embodiments of the hepatic therapeutic actives of the present invention may be effective in treating liver diseases such as hepatitis B (e.g., acute or chronic hepatitis B), hepatitis C (e.g., acute or chronic hepatitis C), cirrhosis, hepatic carcinomas (e.g., hepatocellular carcinoma (HCC)), co-infections of human immunodeficiency virus (HIV) with hepatitis B or hepatitis C, etc., by exhibiting, for example, one or more of: anti-viral effects, anti-retroviral effects, anti-inflammatory effects, cytotoxic effects, anti-neoplastic effects, anti-tumor effects, anti-cancer effects, detoxicant effects, hepatoprotective effects, etc. For example, the use of embodiments of these hepatic therapeutic actives comprising combinations, mixtures, blends, extracts, etc., of these five classes of therapeutically active compounds may be effective in: (1) reducing the effects of chronic hepatitis HBV and hepatitis HCV; (2) improving and reducing symptoms of chronic hepatitis B and hepatitis C, e.g., reducing levels of ALT and AST in patients to healthy levels in, for example, from about 30 to about 60 days; (3) suppressing cirrhosis progress in chronic hepatitis, e.g., improving liver condition of such patients in, for example, from about 30 to about 60 days; (4) eradicating cancerous cells, e.g., reducing the CA 19-9 cancer marker in patients, for example, from about 4000 U/L to about 100 U/L or less after from about 30 to about 60 days of treatment; (5) reducing tumors in patients afflicted with hepatocellular carcinoma (HCC); (6) providing sero-conversion and return of antibody benefits in patients afflicted with hepatitis HBV and/or hepatitis HCV (e.g., for hepatitis B, anti-HBs Ab, for hepatitis C, anti-HCV (EIA-3)), e.g., reducing HBV and HCV to undetectable levels and restoring anti-HBs Ab and anti-HCV (EIA-3) in chronic hepatitis B and C patients; etc. Hepatic anti-viral and cytotoxic activities may be observed when, for example, embodiments of these *Cratoxylum cochinchinense* extracts according to the present invention are administered to patients afflicted with these liver diseases. Embodiments of these *Cratoxylum cochinchinense* extracts according to the present invention may exhibit minimal or no side effects (e.g., rashes, fevers, etc.) when administered, and may also provide a drug delivery system where efficacy of the treatment of the liver disease state may also be improved with using higher doses of the hepatic therapeutic active, shorter treatment periods, with fewer or none adverse side effects compared to other chemotherapy protocols.

Embodiments of the hepatic therapeutic actives of the present invention may also be effective in treating related cancers CA19-9 cancers (i.e., those which may be indicated by the CA19-9 cancer marker) such as gastric cancer, pancreatic cancer, colorectal cancer (colon cancer), bile duct cancer, esophageal cancer, gastro intestinal tract cancer, etc. Embodiments of the hepatic therapeutic actives of the present invention may also be administered in combination with other therapeutic actives such as interferon, peginterferon, ribavirin, other chemotherapy agents (in the case of cancer treatments other than for liver cancer, such as for gastro intestinal tract cancer), etc. Embodiments of the hepatic therapeutic actives of the present invention may also be administered to humans for (e.g., preventative) liver health maintenance regimes.

Embodiments of the hepatic therapeutic actives of the present invention may be administered in any manner suitable to deliver the active ingredient(s) to the patient to treat the liver disease or CA19-9 cancer, or a human to provide liver health maintenance benefits. For administration to patients (e.g., humans), embodiments of the hepatic therapeutic actives of the present invention may be in the form of oral or injectable compositions for administration, while those humans seeking liver health maintenance benefits may orally administer these hepatic therapeutic actives. Embodiments of the hepatic therapeutic actives of the present invention which are orally active may be administered as oral dose forms as tablets, capsules, including sustained or controlled release formulations, pills, powders, granules, elixirs, tinctures, suspensions, syrups and emulsions, may be administered one or more times during the day, e.g., one, two, three, four, etc., times daily, may be administered as orally ingestable compositions comprising, for example, from about 250 to about 750 mg. (e.g., from about 450 to about 550 mg.) of the hepatic therapeutic actives (e.g., as single unit dosages), etc. For oral administration in the form of a tablet or capsule, the hepatic therapeutic active may be combined with an oral, non-toxic, pharmaceutically acceptable, inert carrier such as lactose, starch (e.g., corn starch), sucrose, glucose, methyl cellulose, magnesium stearate, dicalcium phosphate, calcium sulfate, mannitol, sorbitol, etc. For oral administration in liquid form, the hepatic therapeutic active may be combined with any oral, non-toxic, pharmaceutically acceptable inert carrier such as ethanol, glycerol, water and the like. Suitable carriers for oral administration may include but are not limited to amino acid compounds of the type disclosed in U.S. Pat. No. 5,650,386 (Leone-Bay et al.), issued Jul. 22, 1997 and U.S. Pat. No. 5,965,121 (Leone-Bay et al.), issued Oct. 12, 1999, both of which are incorporated by reference. Moreover, when desired or necessary, suitable binders, lubricants, disintegrating agents and coloring agents may also be incorporated into the mixture. Suitable binders may include starch, gelatin, natural sugars such as glucose or β-lactose, corn-sweeteners, natural and synthetic gums such as acacia, tragacanth or sodium alginate, carboxymethylcellulose, polyethylene glycol, waxes, etc. Lubricants used in these dosage forms may include sodium oleate, sodium stearate, magnesium stearate, sodium benzoate, sodium acetate, sodium chloride, etc. Disintegrators may include, without limitation, starch, methyl cellulose, agar, bentonite, xanthan gum, etc.

Oral compositions with enteric coatings may be prepared by mixing the hepatic therapeutic actives with an excipient to form a spheroid, and coating the spheroid with a thin polymer film. For example, the hepatic therapeutic actives may be mixed with non-water swellable microcrystalline cellulose to form a spheroid which may then coated with a film of hydroxypropyl methyl cellulose phthalate and or a plasticizer which prevents any release of the active ingredient in the stomach. When the composition reaches the intestine, the hepatic therapeutic actives may then be released. Other suitable materials for enteric coatings may include, for example, hydroxypropyl methyl cellulose acetate succinate, hydroxypropyl methyl cellulose hexahydrophthalate, shellac, cellulose acetate, cellulose acetate phthalate, polyvinyl acetate phthalate, carboxymethyl ethyl cellulose, methacrylic acid copolymers, methacrylic ester copolymers, etc.

Oral compositions may also be prepared by mixing the hepatic therapeutic actives with a wetting agent such as fatty acid esters, lecithin, sucrose, mannitol or sorbitol, and then spheronizing or granulating the mixture into microgranules. These may then coated with a microporous membrane polymer such as Eudragit® E30D (Rohm Pharma GmbH, Weiterstadt, Germany), hydroxypropyl methyl cellulose phthalate and other wetting agents, plasticizers, etc. These formulations are enteric by nature and the hepatic therapeutic active does not become bioavailable until the system reaches the intestine.

Oral compositions may also be prepared by mixing the hepatic therapeutic actives and an acid such as fumaric or tartaric acid which may be compressed into a spherical tablet and coated with lacquers that are insoluble in gastric juices but soluble in intestinal juices. These lacquers may include copolymers of acrylic acid and methacrylic acid esters, etc. The acidic matrix prevents quick dissolution early and yet promotes the hepatic therapeutic active's bioavailability further downstream in the digestive tract.

Oral compositions may also be prepared by coating a solid dosage form of the hepatic therapeutic actives with hydroxypropyl methyl cellulose phthalate or acidic succinyl and acetyl esters of hydroxypropyl methyl cellulose. Triethylcitrate may be added as a plasticizer which aids in the binding of the coating material to the core pellet. The coating resists dissolution in the stomach but completely dissolves in the small intestine.

In general, embodiments of solid dosage forms comprising the hepatic therapeutic actives may be coated using conventional coating techniques such as conventional pan coating techniques or column spray coating techniques. See PCT application WO 99/38827 (Cook et al.), published Aug. 5, 1999 (herein incorporated by reference) for a more detailed description of these techniques. The hepatic therapeutic actives may also be administered in the form of liposome delivery systems, such as small unilamellar vesicles, large unilamellar vesicles and multilamellar vesicles. The liposomes may be formed from a variety of phospholipids, such as cholesterol, stearylamine, phophatidylcholines (e.g., lecithin), etc. The hepatic therapeutic actives may also be delivered using monoclonal antibodies as individual carriers to which the hepatic therapeutic active molecules may be coupled or the compounds in the hepatic therapeutic actives may be coupled with liver targeting molecules to provide targetable drug carriers (e.g., for the liver). In addition, the compounds in the hepatic therapeutic actives may be coupled to biodegradable polymers that control the release of the active, for example, polylactic acid, polyglycolic acid, copolymers of polylactic and polyglycolic acid, polyepsilon caprolactone, polyhydroxy butyric acid, polyorthoesters, polyacetals, polydihydropyrans, polycynacrylates, cross-linked or amphiphatic block copolymers of hydrogels, etc.

Suitable embodiments of injectable compositions comprising these hepatic therapeutic actives for use in the present invention may be given intravenously, parenterally, intramuscularly, or subcutaneously and may include bolus or extended infusion compositions. Injectable administration of these hepatic therapeutic actives may involve the preparation of suitable infusion solutions according to procedures known to those skilled in the pharmaceutical arts. Administration in these various ways may suitable as long as the beneficial therapeutic effect of the hepatic therapeutic actives is realized by the patient. Such beneficial effect is usually achieved when the target plasma level concentrations of the hepatic therapeutic actives are maintained. Such target plasma level concentrations may be readily determined for each patient by physicians and veterinarians skilled in the art.

The dosage regimen for the hepatic therapeutic actives may be selected in accordance with a variety of factors, including type, species, age, weight, sex, medical condition, etc., of the patient; the particular liver disease or cancer being treated; the severity of the condition to be treated; the routes of administration; the renal and hepatic function of the patient; the particular hepatic therapeutic active to be used, etc. An ordinarily skilled physician or veterinarian may readily determine and prescribe the therapeutically effective amount of the hepatic therapeutic actives required to prevent, counter, or arrest the progress of the liver disease state.

Therapeutic dosages, as well as liver health maintenance dosages, of the hepatic therapeutic actives may be administered in terms of mg. per day, capsules per day, etc. For example, adult patient dosages of from about 2000 to about 4000 mg. of the hepatic therapeutic actives per day, such as from about 2500 to about 3500 mg. of the hepatic therapeutic actives per day (e.g., such as taking two capsules comprising 500 mg of the hepatic therapeutic active thrice daily, resulting in a 3000 mg. per day dosage of the hepatic therapeutic active) may be effective for treating chronic hepatitis B or chronic hepatitis C. For child patients, dosages may reduced to (e.g., such as taking one capsule comprising 500 mg of the hepatic therapeutic active thrice daily, resulting in a 1500 mg. per day dosage of the hepatic therapeutic active). For treating liver cancers such a hepatocellular carcinoma (HCC), as well as other CA19-9 cancers, higher dosages may be required, for example, from about 3500 to about 5500 mg. of the hepatic therapeutic actives per day, such as from about 4000 to about 5000 mg. of the hepatic therapeutic actives per day (e.g., such as taking three capsules comprising 500 mg of the hepatic therapeutic active thrice daily, resulting in a 4500 mg. per day dosage of hepatic therapeutic active). For providing a liver health maintenance regime, adult humans, for example, may take the hepatic therapeutic active in dosages of from about 500 to about 2000 mg. per day (e.g., such as taking one or two capsules once or twice daily). To provide a therapeutic benefit, the hepatic therapeutic actives may be administered to the patient afflicted with the liver disease or CA19-9 cancers for a period of for example, at least about 30 days, such for from about 30 to about 60 days. For those seeking a liver health maintenance regime, the hepatic therapeutic actives may be taken for a period of, for example, at least about 30 days, and for as long as the liver health maintenance regimes is desired.

Embodiments of the hepatic therapeutic actives of the present invention may be administered in admixture with suitable pharmaceutical diluents, excipients or carriers (collectively referred to hereafter as "pharmaceutical carriers"), suitably selected with respect to the intended form of administration, such as oral tablets, capsules, elixirs, syrups, etc., and consistent with conventional pharmaceutical practices. See, for example, Remington, *The Science and Practice of Pharmacy* (2000, 20$^{th}$ Ed., Mack Publishing Company), the entire contents and disclosure of which is herein incorporated by reference, for suitable pharmaceutical carriers known to those skilled in the art. Injectable compositions suitable for use herein are known to those skilled in the pharmaceutical arts. For example, injectable compositions may include aqueous solutions, syrups, aqueous or oil suspensions and emulsions with edible oil, including cottonseed oil or peanut oil. Suitable dispersing or suspending agents for aqueous suspensions may include synthetic or natural gums, such as tragacanth, alginate, acacia. dextran, sodium carboxymethyl cellulose, gelatin, methylcellulose and polyvinylpyrrolidone. These injectable compositions may include a sterile aqueous or nonaqueous solvent, in particular water, isotonic saline, isotonic glucose solution, buffer solution or other solvent conveniently used for parenteral administration of active pharmaceutical ingredients, or can be provided as a sterile freeze-dried powder, which is readily dissolved in a sterile medium immediately prior to use. These injectable compositions may be formulated as long acting depot preparations for subcutaneous or intramuscular implantation, and may include suitable polymeric or hydrophobic emulsions in the pharmaceutical carrier.

Suitable injectable (e.g., intravenous) solutions may include pharmaceutically acceptable pH buffers (e.g., sodium citrate), tonicity adjusting agents and other components providing a storage stable and therapeutically effective injectable solution. Tonicity adjusting agents, including sodium chloride, may be used to adjust tonicity for osmotic pressure and to prevent blood cell lysing. These agents may minimize pain experienced by patients receiving intravenous administrations of pharmaceutical compositions. The amount used is that which makes the formulation isotonic with the osmotic pressure of the biological system of the patient. Expressed in osmolarity units, the amounts of tonicity adjusting agent suitable for use (e.g., sodium chloride) may be from about 50 to about 500 milliosmoles, such as about 290 milliosmoles. For injectable compositions, pharmaceutically acceptable osmolarity may be achieved by formulating with an amount of sodium chloride of from about 1.5 to about 15 mg/ml, such as about 9 mg/ml. Such osmolality may also be achieved by using an amount of mannitol of from about 7 to about 75 mg/ml, such as about 50 mg/ml. Other tonicity adjusting agents which may be used to adjust tonicity include, but are not limited to, dextrose and other sugars. These injectable compositions may also be suitable for long-term storage in glass containers commonly used in the pharmaceutical industry, e.g., in concentrated form in standard USP Type * borosilicate glass containers.

In general, the method for preparing embodiments injectable compositions comprising the hepatic therapeutic actives may involve combining the various ingredients in a mixing vessel, e.g., at room temperature. The hepatic therapeutic actives (in salt or free base form), buffers sources (e.g., citric acid and sodium citrate), and tonicity adjusting agent(s), may be combined to obtain an active concentration, for example, in the range of from about 0.01 mg/ml to about 1 mg/ml. In one embodiment for preparing such compositions, a substantial portion of the finished product amount of water (for example, from about 60 to 100%) may be introduced into a standard pharmaceutical mixing vessel. An amount of the hepatic therapeutic actives suitable for obtaining the desired finished product concentration is dissolved in the water. Amounts of sodium citrate and citric acid sufficient to obtain a finished citrate concentration of from about 2 to about 20 mM, are added. A pharmaceutically acceptable amount of tonicity adjusting agent in the isotonic range may be added. Any remaining portion of water may then be added to achieve the desired final concentrations of ingredients. The amount of water initially used in preparing the formulation, and the amount of the remaining portion of water added at the end of the procedure, does not affect the properties of the finished product. Such amounts may be a matter of choice for those skilled in the pharmaceutical arts, allowing for pH adjustment during formulation. Concentrated formulations of these injectable compositions may be diluted at the time of administration with a suitable diluent to obtain a finished concentration, for example, of about 0.05 mg/ml, which may be suitable for transfer to an infusion bag and use by a patient in need of the treatment.

The hepatic therapeutic actives may also be formulated for intranasal delivery, sublingual delivery (i.e., under the tongue), etc. The hepatic therapeutic actives may also be formulated for delivery through a transdermal patch, as a rectal suppository, etc.

The hepatic therapeutic actives (with or without pharmaceutical carriers) may also be formulated as a therapeutic composition or packaged drug product that is provided with a set of instructions for administering the composition/drug to treat a patient in need thereof. The set of instructions may be written or printed on a sheet of paper, may be on the packaging associated with the packaged drug (e.g., on the package label), may be in the form of electronic media or software (e.g., in the form of a floppy disk(s), CD ROM disk(s) or other non-volatile electronic storage media) that may be loaded, installed (directly or by downloading from a remote site such as via a LAN, WAN or the Internet), or otherwise may be read by a computer, personal digital assistant (PDA) or other electronic device, or any other suitable method for providing instructions on how to administer the composition/active to treat the patient.

EXAMPLES

Extract Preparation for Test Samples

The dried stem, bark and roots of the *Cratoxylum cochinchinense* plant are extracted three different times at room temperature using different solvents. In the first (aqueous) extraction, these plant materials are extracted using water (ratio of plant materials:water=1:10, w/v) for 30 min. at a boiling temperature to provide a first filtrate comprising tocotrienols and oleanolic triterpenoids. In the second (polar organic solvent) extraction, the residual plant materials from the first extraction are extracted again using ethanol (ratio of plant materials:ethanol=1:40, w/v) for 60 min to provide a second filtrate comprising acridones, xanthones, and thioxanthones. In the third (non-polar organic solvent) extraction, the residual plant materials from the second extraction are extracted again using hexane (ratio plant materials:hexane=1:3, v/v) for 60 min to provide a third filtrate comprising acridones, xanthones, thioxanthones, tocotrienols, and oleanolic triterpenoids. The three filtrates resulting from these three extractions are then combined together and subsequently lyophilized (freeze dried) at −25° C. to provide a hepatic therapeutic active comprising about 30% (±5%) acridone, about 20% (±5%) xanthone, about 40% (±5%) thioxanthone, about 5% (+2%) delta-tocotrienol, and about 5% (±2%) oleanolic triterpenoid. Test samples are prepared by entirely dissolving this lyophilized hepatic therapeutic active in 80% ethanol.

Therapeutic Treatment of Patients with Test Samples

Six human patients afflicted with chronic hepatitis B, eight human patients afflicted with chronic hepatitis C, and five human patients afflicted with hepatocellular carcinoma (HCC) are used in therapeutic evaluation. Each of the fourteen hepatitis B or C patients orally ingest two 500 mg. capsules of the test samples three times daily for 30 days. Each of the five HCC patients orally ingests three 500 mg. capsules of the test samples three times daily for 30 days.

The results (before and after treatment) for the hepatitis B patients and the hepatitis C patients are shown in Tables 1 through 4 below:

TABLE 1

Characteristics of Hepatitis B Patients Before Treatment

| Factor | Mean Value of 6 Patients |
|---|---|
| AST | 152 U/L[1] |
| ALT | 407 U/L[2] |
| HbsAg | Positive |
| HbeAg | Positive |
| HBV DNA | Positive |
| Anti-HBs Ab | Negative |

[1]Normal-<41
[2]Normal-<51

TABLE 2

Characteristics of Hepatitis B Patients After Treatment

| Factor | Mean Value of 6 Patients |
|---|---|
| AST | 8 U/L[1] |
| ALT | 15 U/L[2] |
| HbsAg | Negative |
| HbeAg | Negative |
| HBV DNA | Not Detected |
| Anti-HBs Ab | Positive |

[1]Normal-<41
[2]Normal-<51

TABLE 3

Characteristics of Hepatitis C Patients Before Treatment

| Factor | Mean Value of 8 Patients. |
|---|---|
| AST | 175 U/L[1] |
| ALT | 503 U/L[2] |
| Anti-HCV (EIA-3) | Positive |
| HCV RNA | 882000 |

[1]Normal-<41
[2]Normal-<51

TABLE 4

Characteristics of Hepatitis C Patients After Treatment

| Factor | Mean Value of 6 Patients. |
|---|---|
| AST | 6 U/L[1] |
| ALT | 14 U/L[2] |
| Anti-HCV (EIA-3) | Positive |
| HCV RNA | Not Detected |

[1]Normal-<41
[2]Normal-<51

As shown in Tables 1 and 3 above, the hepatitis B and C patients before treatment with the test samples may be characterized as having elevated levels of the factors (i.e., AST, ALT, HBsAg, HBeAg HBV DNA, Anti-HCV (EIA-3), and HCV RNA) which were evaluated for each patient category. By contrast, as shown in Tables 2 and 4, after treatment with the test samples, the hepatitis B and C patients may be characterized as having greatly reduced levels of these factors.

Figure 1:
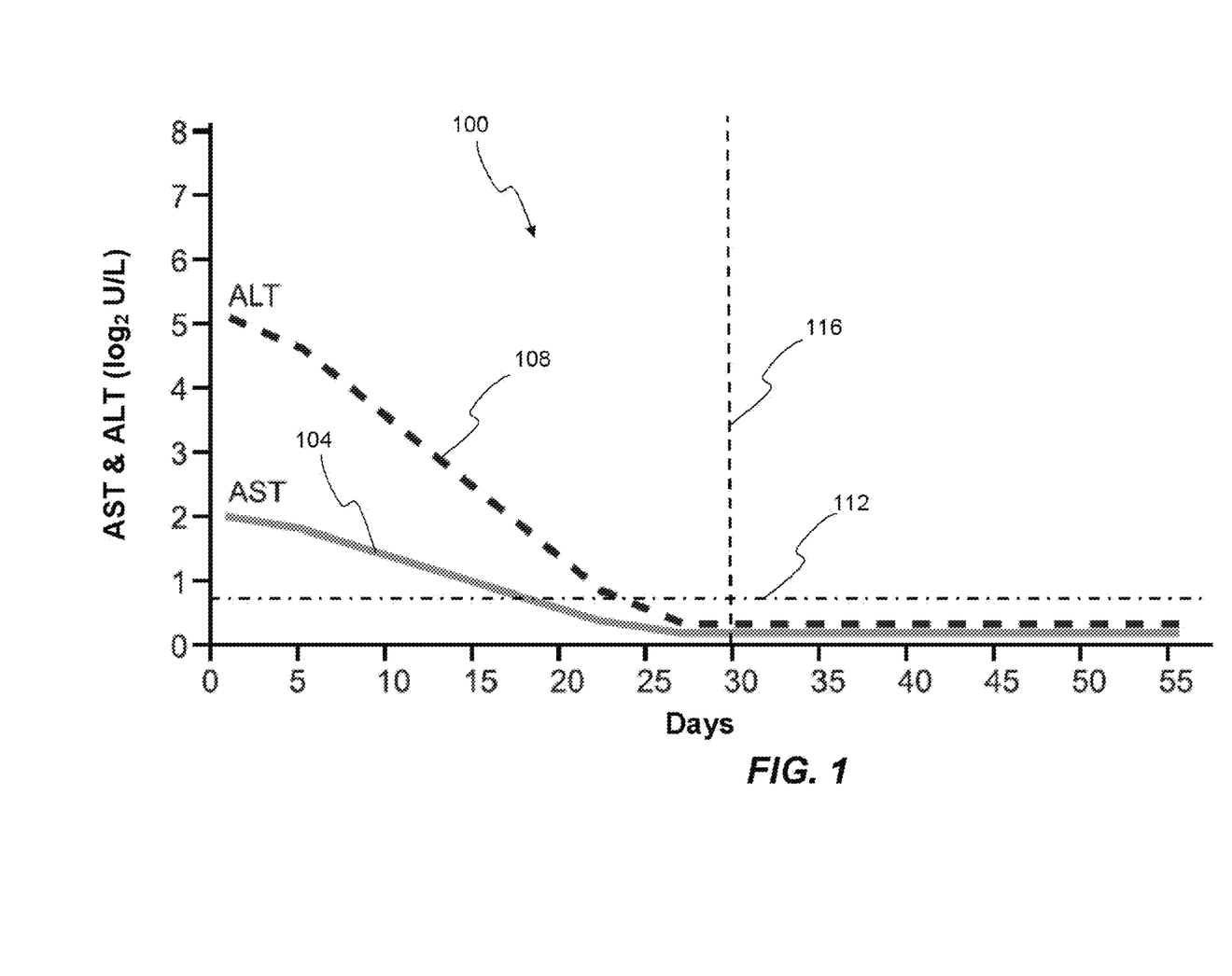
FIG. 1 provides graphical plots of AST and ALT values ($\log_2$ U/L) versus days of treatment of six hepatitis B human patients with test samples of a lyophilized hepatic therapeutic active extracted from the *Cratoxylum cochinchinense* plant.

FIG. 1 provides graphical plots, indicated generally as 100, of AST and ALT values (in terms $\log_2$ U/L) versus days of treatment of the hepatitis B patients with the test samples. AST values are plotted as solid line 104, while ALT values are plotted as dashed line 108. Horizontal dashed line 112 and below represents normal AST and ALT values. Vertical dashed line 116 indicates the end of the 30 day treatment period. As shown by FIG. 1, the factors AST and ALT may be characterized as being significantly reduced after 30 days of treatment with the test samples.

Figure 2:
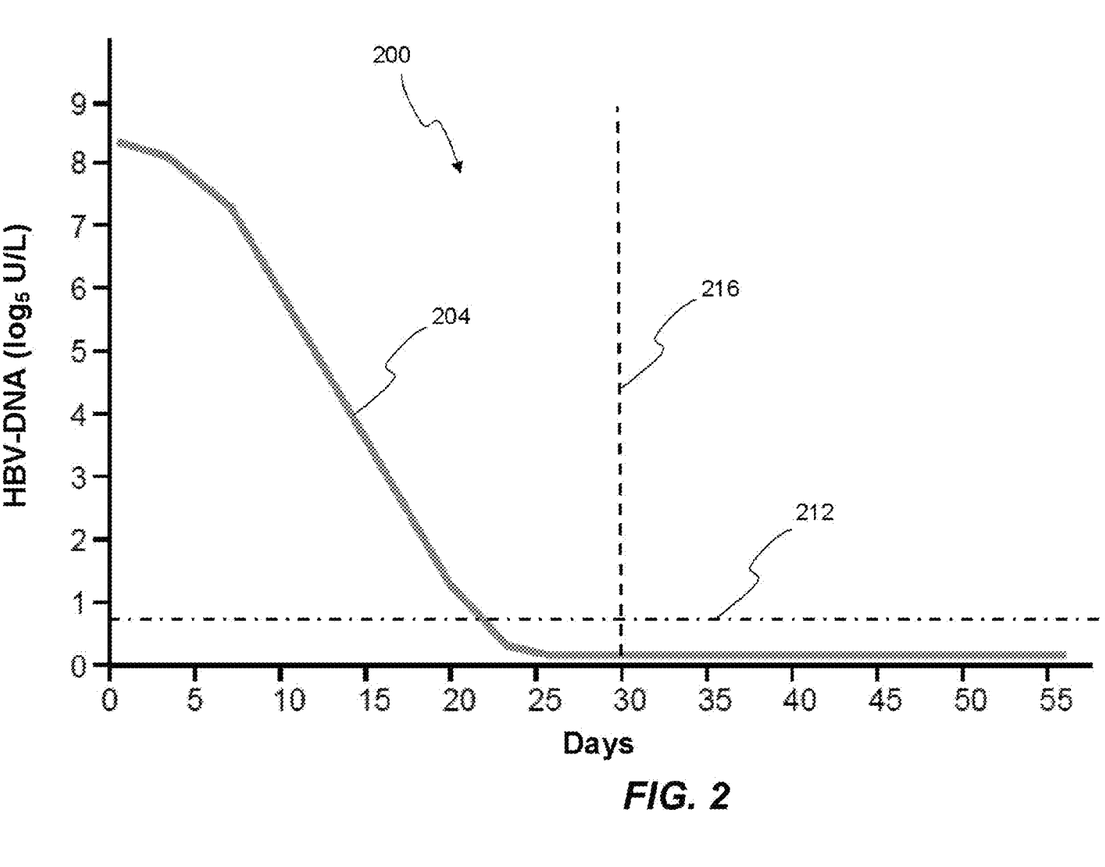
FIG. 2 provides a graphical plot of HBV-DNA values ($\log_5$ U/L) versus days of treatment of six hepatitis B human patients with the same test samples.

FIG. 2 is a graphical plot, indicated generally as 200, of HBV-DNA values ($\log_2$ U/L) versus days of treatment of the hepatitis B patients of the test samples. Plotted HBV-DNA values are represented by solid line 204. Horizontal dashed line 212 and below represents normal HBV-DNA values. Vertical dashed line 216 indicates the end of the 30 day treatment period. FIG. 2 shows, after 30 days of treatment with the test samples, decreasing HBV-DNA values as reflected by line 204, and thus indicating sero-conversion (reduction) of the antigens HBsAg, and HBeAg, as well as the production of the antibody anti-HBsAb.

Figure 3:
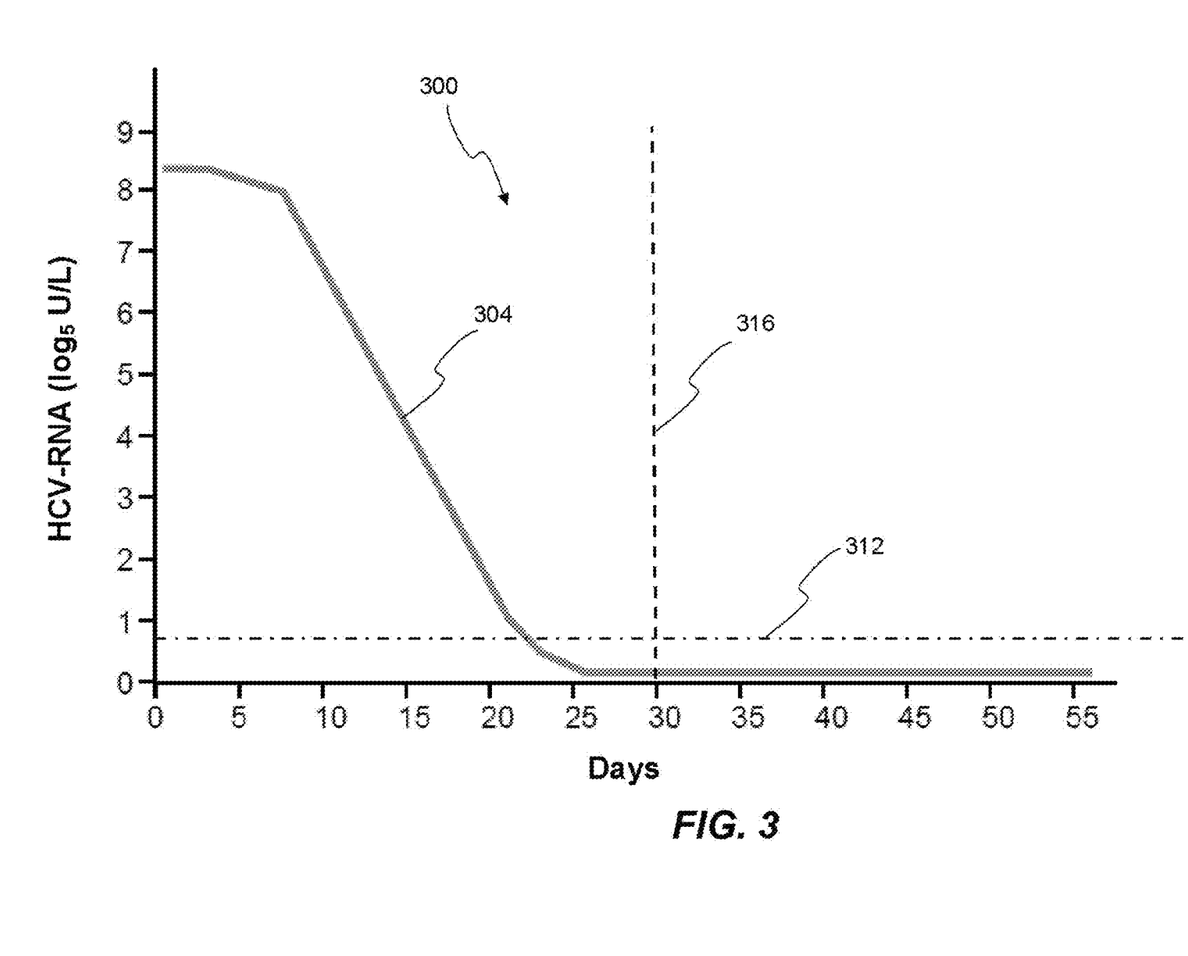
FIG. 3 provides a graphical plot of HCV-RNA values ($\log_5$ U/L) versus days of treatment of eight hepatitis C human patients with the same test samples.

FIG. 3 provides a graphical plot, indicated generally as 300, of HCV-RNA values ($\log_g$ U/L) versus days of treatment of the hepatitis C patients with the test samples. Plotted HCV-RNA values are represented by solid line 304. Horizontal dashed line 312 and below represents normal HCV-DNA values. Vertical dashed line 316 indicates the end of the 30 day treatment period. FIG. 3 shows, after 30 days of treatment with the test samples, a lowering of the HCV-RNA viral load of hepatitis C patients as reflected by line 304, thus reducing liver inflammation and fibrosis in those patients, as well as achieving normal AST and ALT levels.

Figure 4:
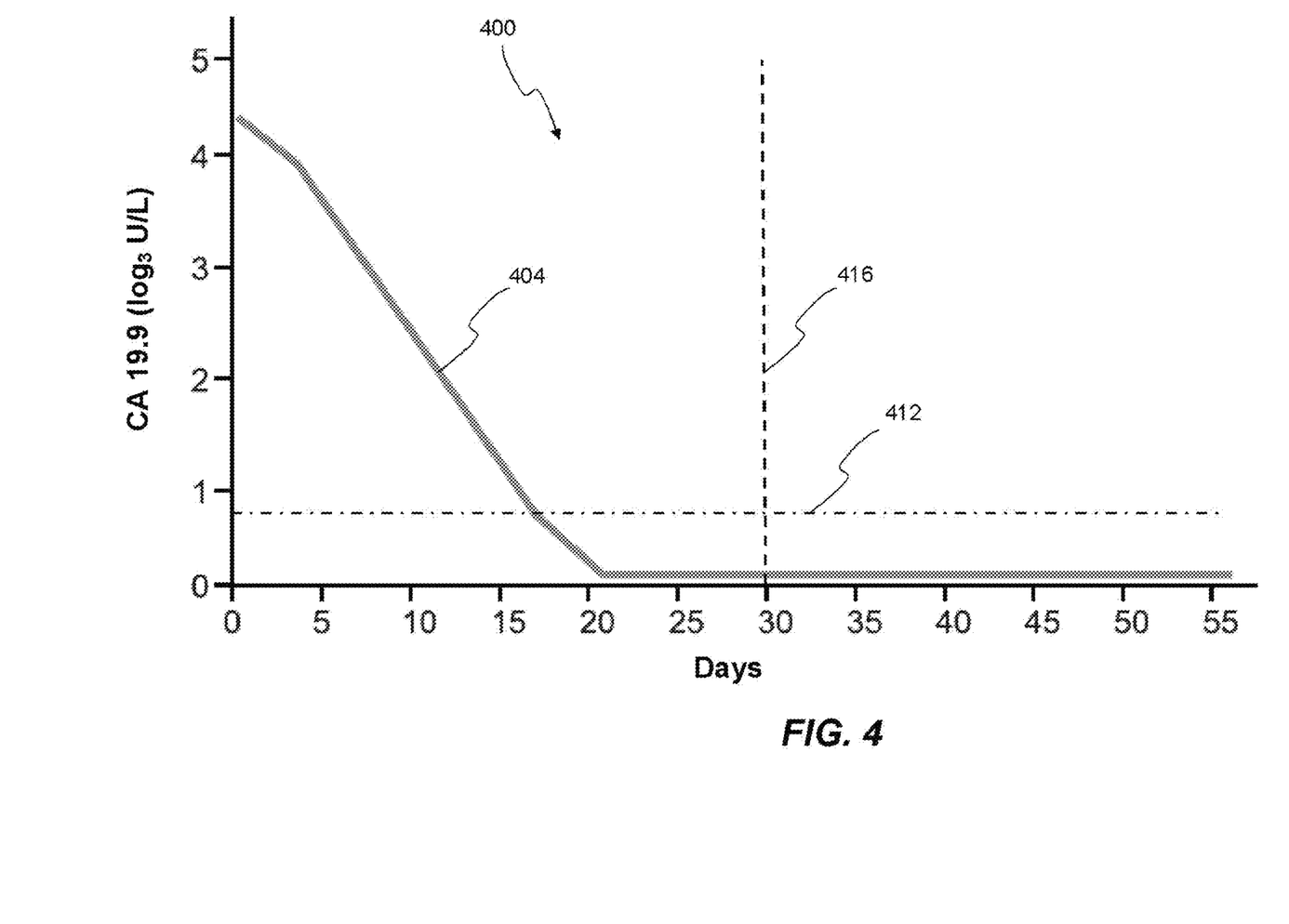
FIG. 4 provides a graphical plot of CA19-9 cancer marker values ($\log_3$ U/L) versus days of treatment of five hepatocellular carcinoma (HCC) human patients with the same test samples.

For the five patients afflicted with hepatocellular carcinoma (HCC), a liver biopsy is performed to determine the severity of hepatic lesions, the extent of necrosis and inflammation, and the degree of fibrosis and any associated lesions. For these five patients, FIG. 4 provides a graphical plot, indicated generally as 400, of CA19-9 cancer marker values ($\log_3$ U/L) versus days of treatment of these HCC patients with the test samples. Plotted CA 19-9 cancer marker values are represented by solid line 404. Horizontal dashed line 412 and below represents normal CA19-9 cancer marker values. Vertical dashed line 416 indicates the end of the 30 day treatment period. As shown in FIG. 4, before treatment, the CA19-9 cancer marker is found to be above 4000 U/L. As also shown in FIG. 4, after 30 days of treatment with the test samples, the CA19-9 cancer marker is found to be less than 100 U/L.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A method of treating hepatocellular carcinoma (HCC) in a patient comprising administering
a hepatic therapeutic active comprising a *Cratoxylum cochinchinense* extract comprising, by weight of the hepatic therapeutic active: from about 28 to about 32% of one or more acridone compounds; from about 18 to about 22% of one or more xanthone compounds; from about 32 to about 42% of one or more thioxathone compounds; from about 3 to about 7% of one or more tocotrienol compounds; and from about 3 to about 7% of 3-hydroxy-23-sulfoxy-olean-12-en-28-oic acid; to a patient in need thereof, a therapeutic amount of the hepatic therapeutic active.

2. The method of claim 1, wherein the hepatic therapeutic active is administered in an amount of from about 3500 to about 5500 mg. per day to the patient for a period of at least about 30 days.

3. The method of claim 2, wherein the hepatic therapeutic active is administered in an amount of from about 4000 to about 5000 mg. per day to the patient for a period of from about 30 to about 60 days.

4. The method of claim 1, wherein the hepatic therapeutic active is administered to the patient in need thereof in combination with a pharmaceutically acceptable carrier.

5. The method of claim 1, wherein the acridone compounds comprise one or more of: acridone or acridone acetic acid.

6. The method of claim 1, wherein the xanthone compounds comprise one or more of: xanthone; 5-O-methyl-celebixanthone; celebixanthone; 1,3,7-trihydroxy-2,4-di(3-methylbut-2-enyl)xanthone; cochinchinone A; alpha-mangostin; beta-mangostin; or cochinchinone.

7. The method of claim 1, wherein the thioxanthone compounds comprise one or more of: thioxanthone; or the thio analogs of 5-O-methylcelebixanthone, celebixanthone, 1,3,7-trihihydroxy-2,4-di(3-methylbut-2-enyl)xanthone, cochinchinone A, alpha-mangostin, beta-mangostin, and cochinchinone.

8. The method of claim 1, wherein the tocotrienol compounds comprise one or more of: alpha-tocotrienol; beta-tocotrienol; gamma-tocotrienol; or delta-tocotrienol.

* * * * *